United States Patent [19]

Fedter et al.

[11] Patent Number: 4,793,175

[45] Date of Patent: Dec. 27, 1988

[54] HUMIDITY SENSOR, SENSOR MATERIAL, METHOD OF MANUFACTURE AND HUMIDITY SENSING SYSTEM, ESPECIALLY FOR AUTOMOTIVE USE

[75] Inventors: Horst Fedter, Bühlertal; Werner Grünwald; Manfred Köder, both of Gerlingen; Peter Nolting, Bühlertal; Claudio De La Prieta, Stuttgart; Kurt Schmid, Ditzingen-Schöckingen, all of Fed. Rep. of Germany

[73] Assignee: Robert Bosch GmbH, Stuttgart, Fed. Rep. of Germany

[21] Appl. No.: 28,715

[22] Filed: Mar. 20, 1987

[30] Foreign Application Priority Data

Apr. 5, 1986 [DE] Fed. Rep. of Germany ....... 3611468
Apr. 16, 1986 [DE] Fed. Rep. of Germany ....... 3612726
Jul. 24, 1986 [DE] Fed. Rep. of Germany ....... 3625071

[51] Int. Cl.$^4$ ............................................. G01N 19/10
[52] U.S. Cl. ........................................ 73/73; 73/336.5; 252/963
[58] Field of Search ............... 73/73, 336.5, 336, 335; 324/65 R; 252/963

[56] References Cited

U.S. PATENT DOCUMENTS

| | | | |
|---|---|---|---|
| 4,041,437 | 8/1977 | Matsuura et al. | 73/73 X |
| 4,080,564 | 3/1978 | Nitta et al. | 324/65 R |
| 4,119,909 | 10/1978 | DeBerry | 324/65 R X |
| 4,142,148 | 2/1979 | Johansson | 324/65 R X |
| 4,464,647 | 8/1984 | Yokomizo et al. | 73/336 X |
| 4,497,701 | 2/1985 | Murata et al. | 73/335 X |
| 4,546,916 | 10/1985 | Tsuaki | 73/336.5 X |
| 4,642,601 | 2/1987 | Sugawara et al. | 73/336.5 X |

Primary Examiner—Stuart S. Levy
Assistant Examiner—Joseph J. Hail III
Attorney, Agent, or Firm—Frishauf, Holtz, Goodman & Woodward

[57] ABSTRACT

An ion conductive sensor is connected to a current source which, in order to prevent polarization effects, controls current flow through the sensor in spaced or polarity-alternating pulses. If the sensor is a humidity sensor, it is preferably constituted by $Cr_2O_3$, $V_2O_5$ and $Na_2WO_4$ in a proportion, by weight, of preferably 2 to 2.5:1:1, sintered on a substrate which has comb electrodes applied thereto. The sensor is especially immune to noise or disturbance pulses from the current supply and is especially suitable for use as an ambient humidity sensor in an automotive vehicle (810).

29 Claims, 6 Drawing Sheets

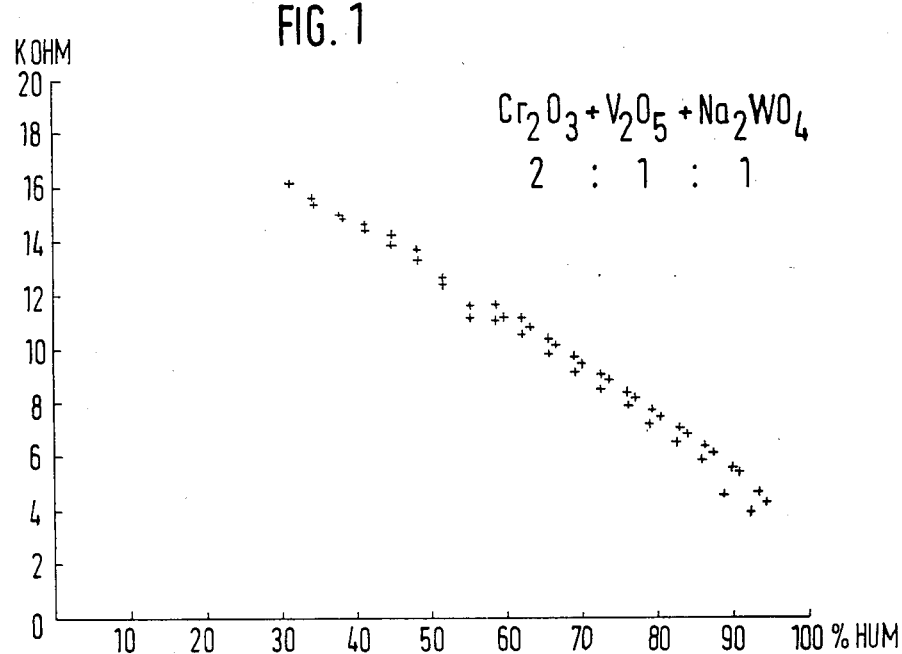
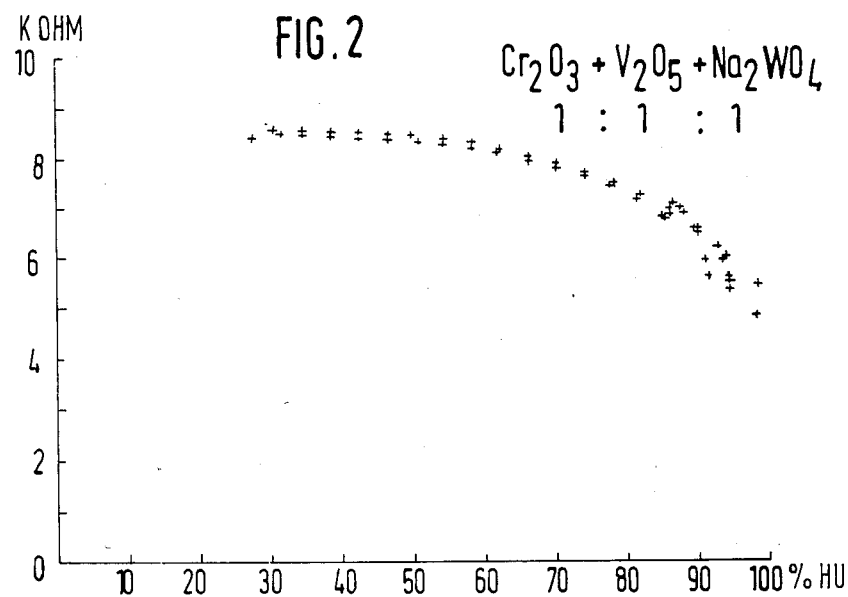

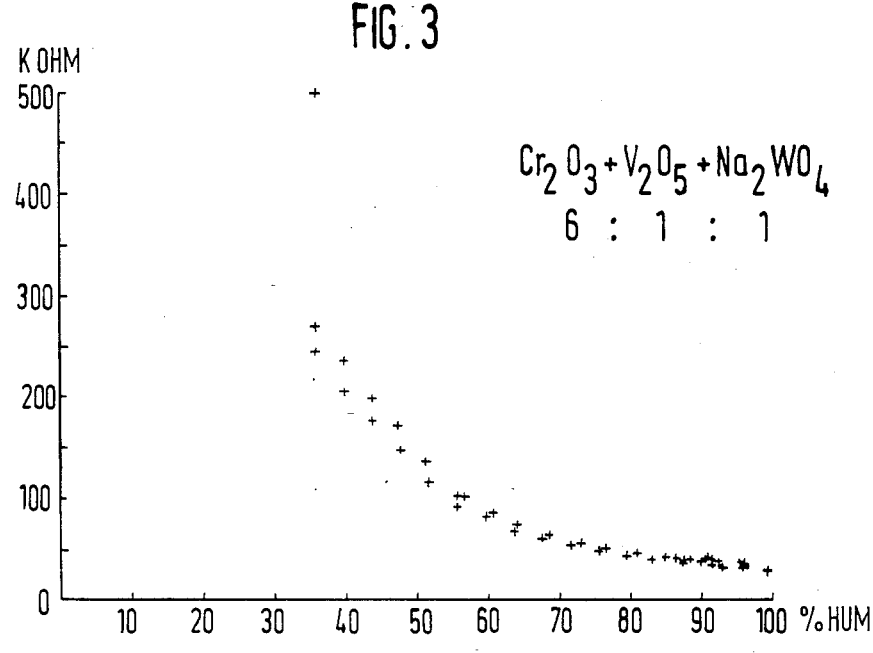
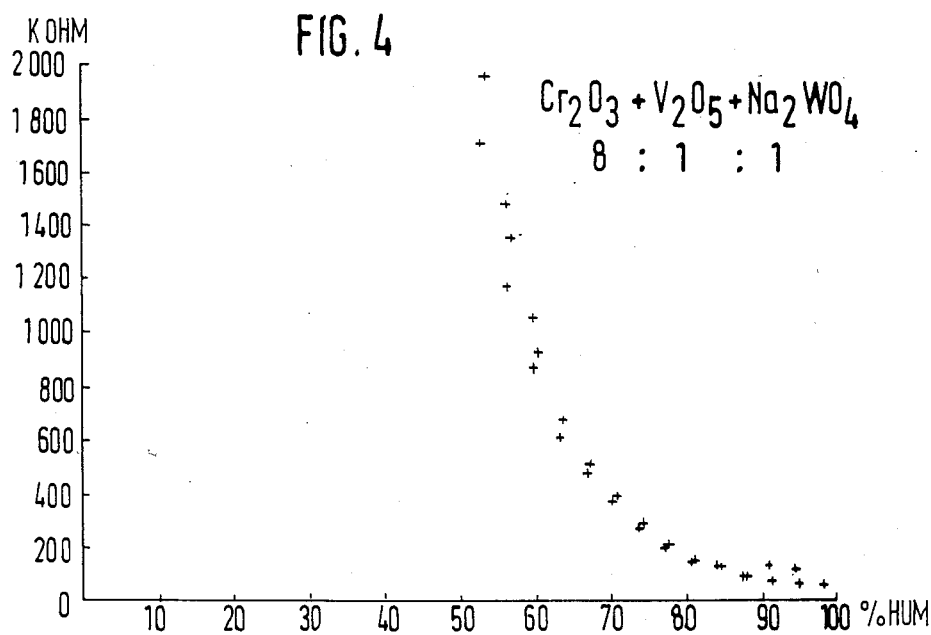

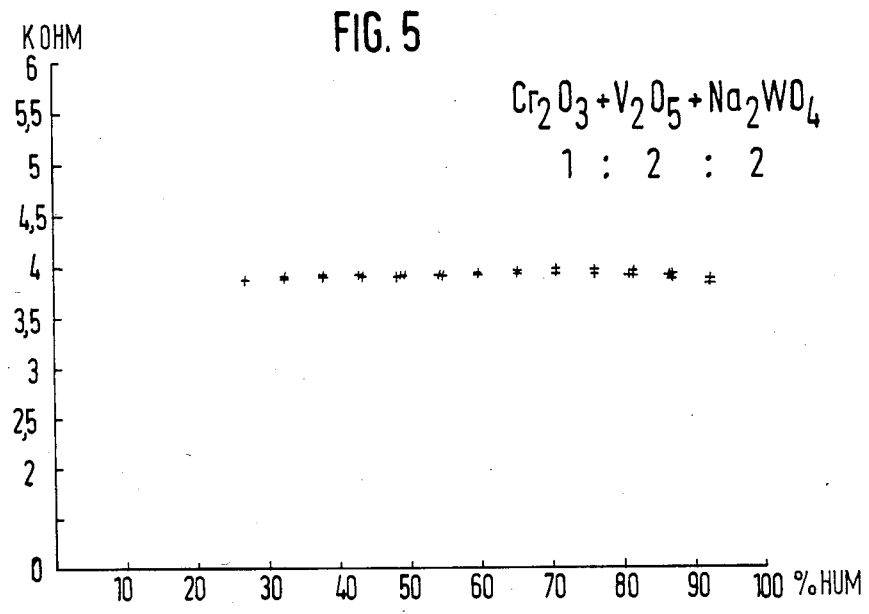
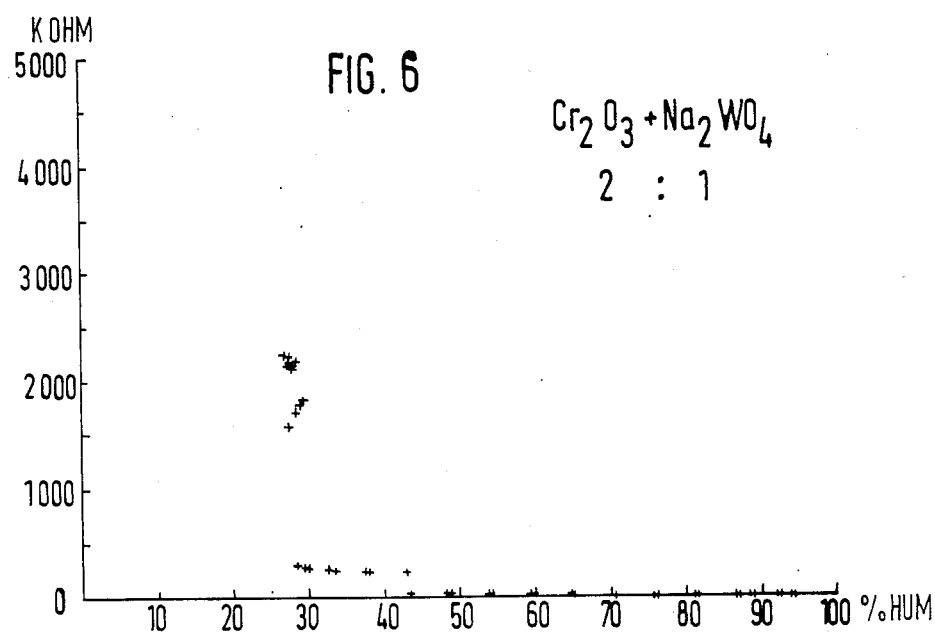

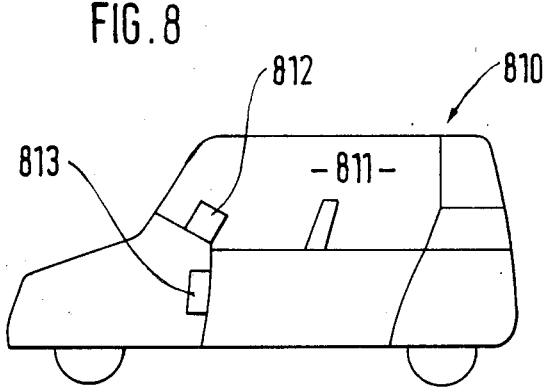
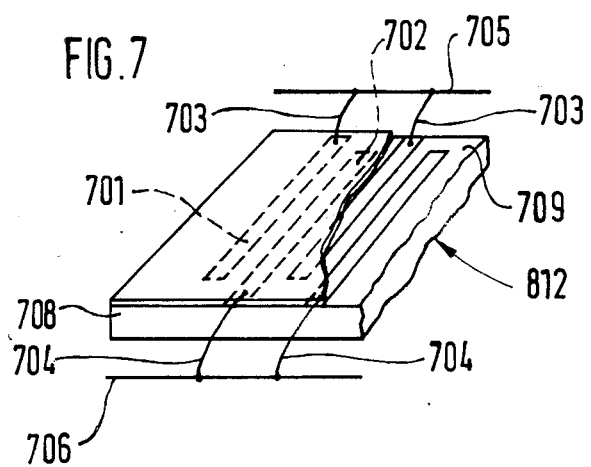

HUMIDITY SENSOR, SENSOR MATERIAL, METHOD OF MANUFACTURE AND HUMIDITY SENSING SYSTEM, ESPECIALLY FOR AUTOMOTIVE USE

The present invention relates to sensing ambient humidity, and more particularly sensing the percentage humidity within an enclosed space, for example the passenger compartment of an automotive vehicle.

BACKGROUND

Humidity sensors which utilize a metal oxide ceramic semiconductor element, in which the ion conductivity changes upon absorption of water or water vapor, are known. One such structure is described in European Patent No. EP-A-33 521. The conductivity of the sensor is measured in an electrical circuit. Polarization effects at the electrodes of the sensors should be avoided and, thus, measuring the conductivity of the sensor with direct current is not possible if the application of direct current extends for an appreciable period of time. The European Patent 33 521 describes a sensor which is serially connected with an alternating current source and electrical resistor. The alternating voltage measured across the resistor will be representative of relative humidity. The alternating voltage measured signal is converted into a d-c signal in a rectifier. The system requires an alternating current generator or a bipolar supply source. Operating such a sensor from a d-c source, for example a vehicle battery, thus is not possible without additional circuitry. The disadvantage of requiring a bipolar supply source is particularly serious in battery-operated circuits since an electrical center or neutral terminal can be obtained only with additional circuit components, which introduce losses and further introduce complexity and are sources of malfunction.

British Patent No. 1,422,182 describes a humidity sensor which is made of $Cr_2O_3$ and $V_2O_5$. The proportion—by weight—of the components is 1:1. The sensor is constructed in form of a small globule or pearl, and sintered at 1550° C. When finished, the resistance is comparatively. Constructing such a sensor is complex, and the high internal resistance reduces the measuring sensitivity thereof. Further, it has been found in actual operation that such sensors are sensitive to interference or disturbance pulses. Disturbance pulses and switching pulses and variations in supply circuit voltage, including peaks which occur upon sudden switching ON and switching OFF of loads occur, however, frequently in automotive vehicles.

THE INVENTION

It is an object to provide a humidity sensing simple, can readily be operated from a unipolar voltage source, such as a battery, and especially a vehicular battery; and to provide a sensor, sensor material, method of making it, and an application circuit, in other words an entire sensor system, from initial manufacture of the sensor to the eventual application thereof.

Briefly, and in accordance with a feature of the invention, the relative humidity sensor, in which the resistance of the sensor changes upon change of ambient humidity, is made by applying electrodes, for example in interdigited, comb form on a substrate, preferably of ceramic material, and applying a sensor mixture, for example in form of a thickfilm printable paste, on the substrate carrier. In accordance with a feature of the invention, a homogenized mixture of $Cr_2O_3$, $V_2O_5$ and $Na_2WO_4$ is presintered, and, to the presintered mixture, a glass paste is added to form an application paste which, then, can be applied to the substrate on which the electrodes have been previously applied. The application paste on the substrate is then sintered together. Preferably, the relationship of the component of the mixture, by weight, is 2.5:1:1, presintering is carried out at about 550° C., and the sintered mixture is then ground to a powder. The glass paste may have a thinner added thereto in order to provide a paste which can be applied by thick-film technology. A suitable substrate is $Al_2O_3$. Final sintering is carried out, preferably, at about 850° C.

In accordance with a feature of the invention, the homogenized mixture which responds readily to changes in relative humidity by changing its resistance has as a base a ceramic material of $Cr_2O_3$ and $V_2O_5$ and, additionally, and in accordance with a feature of the invention, contains a substantial proportion of $Na_2WO_4$. The ratio of the components, by weight, can be varied somewhat, for example can be from 1.5 to 3:1:1.

A humidity sensor so made and resulting from the described process is particularly suitable to sense humidity within an automotive vehicle, for example in the passenger compartment thereof. When the humidity reaches a predetermined level—as determined by a predetermined change of resistance of the sensor, a fan, heater, or dehumidifier, typically the air-conditioning system of the vehicle, may be automatically energized. Thus, fogging of windows and, for safety most importantly, fogging of the windshield and rear window can be effectively prevented.

In accordance with a further feature of the invention, and to permit operation of the sensor, without polarization effects from a direct current source, current is applied to the sensor in cyclically sequential pulses, the current being, preferably, derived from a constant current or constant voltage source. Preferably, the polarity of the energy supplied to the sensor is changed, cyclically, while the current or voltage being supplied is controlled, so that the current supply or voltage across the sensor or a sensing system will be maintained at a predetermined level, so that changes in resistance of the sensor can be easily evaluated. The switching network for electrical energy supply at predetermined, constant voltage or current can easily be made by including controlled switches, for example semiconductor switches as part of the energy supply source or in the connections from the energy supply source to the sensor itself.

The sensing system has the advantage that sensors made of the material and in accordance with the invention can be manufactured easily and in large quantities at low cost. The sensor has a comparatively low resistance resulting in high measuring sensitivity and also then being essentially immune to interference or noise pulses or disturbances within the supply. The change in resistance of the sensor with respect to relative humidity is essentially linear, which substantially facilitates evaluating the sensor signals.

The humidity sensing system has the additional advantage that energy supply and the circuitry in connection with a voltage source without a center tap can be easily provided. The sensor will not exhibit polarization effects when it is energized in pulses, either of unchanging polarity with intervening gaps, or in pulses with or without intervening gaps, in which the pulses alternate in polarity.

Use of a constant current source to generate the pulses measuring current has the additional advantage that the measured signal or sensed signal can be sensed directly across the humidity sensor, so that no further serial sensing resistors are necessary. The current supplied by the constant current source is applied to the sensor, preferably with changing polarity. The duty cycle, that is, the pulse-pause relationship, and the alternating cycle or frequency of alternating pulses preferably should be controllable. An electrically controlled switch is connected in circuit with the constant current source and the sensing element which commands the application of the respective pulses. Of course, the constant current source itself can be constructed to switch ON and OFF, with same or changing polarity, for example by use of a multivibrator circuit. Preferably, current pulses at the same time control a sensing circuit which includes a sample-and-hold circuit to obtain a measuring signal. The method, sensor, sensor circuit, that is, the respective features of the inventive system, are particularly suitable in applications in which a supply voltage for supply of electrical energy of only a single polarity is provided, for example by an automotive-type battery. Drawings FIGS. 1 to 6 are graphs which illustrate the change in resistance (ordinate) in kilo ohms with change in percent humidity (abscissa), with different materials, at different weight ratios;

FIG. 7 is a perspective schematic view of a sensor structure, partly broken away, and illustrating the substrate, electrodes, and ceramic cover layer of the materials in accordance with the present invention;

FIG. 8 illustrates the use and placement of a sensor within the passenger compartment of a motor vehicle, connected to an evaluation circuit;

DETAILED DESCRIPTION

Figure 9:
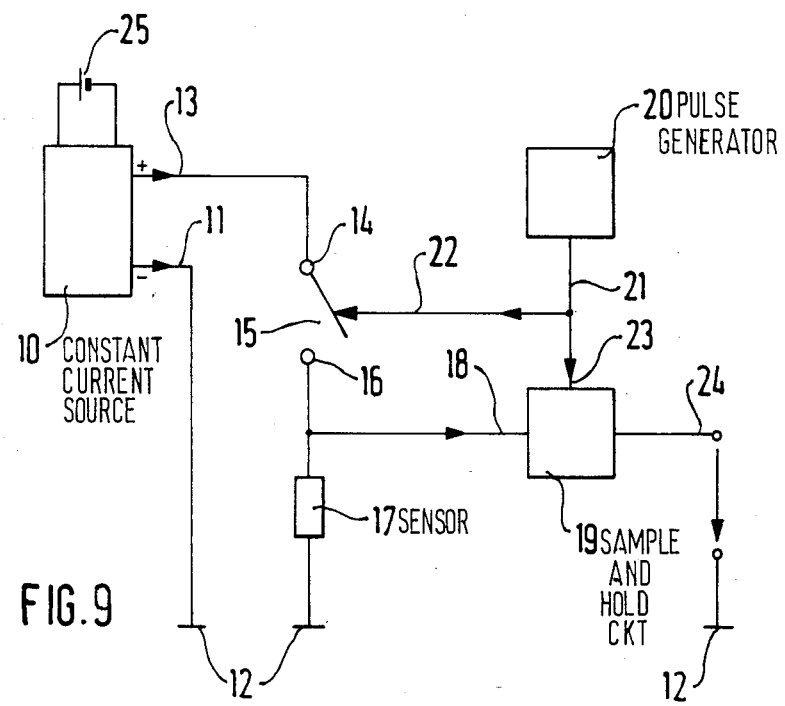
FIG. 9 is a schematic circuit diagram for energizing the sensor of FIG. 7.

The invention will be described, first, by describing a sensor element, and its method of manufacture, as well as its composition, and thereafter the sensor in an energization circuit.

Structure and Composition of Sensor, and Method of its Manufacture

Three components $Cr_2O_3$, $V_2O_5$ and $Na_2WO_4$ are premixed in a ratio—by weight—of 2.5:1:1. The mixture is placed into a powder mill and there homogenized. Thereafter, the homogenized mixture is presintered for about an hour at about 550° C. The presintered mixture is again milled in a powder mill. The particle size should be at about 1 micrometer. About 10%—by weight—of a glass paste is then added to the homogenized, pulverized mixture. The glass paste forms a binder. A glass paste of the type 4011C of Electro Science Laboratory (ESL) has been found particularly suitable. The resulting paste may have a thinner added thereto, if desired, so that a printable paste will result. Suitable thinners are benzyl alcohol and terpineol. Preferably, printing is carried out by well known thick-film technology.

A substrate 708, for example of aluminum oxide and of a dimension of 6×50 mm, is provided on which electrodes 701, 702 are applied, in interdigited form. The electrodes are conducted to respective electrode buses 705, 706 by bonding wires 703, 704, respectively. Of course, the buses can be applied directly on the aluminum oxide substrate 708, and externally connected at terminal ends of the substrate 708, as well known. The illustration of FIG. 7 is merely to serve as an example. The electrodes 701, 702 are double-comb-like interdigited made, for example of platinum, gold, or a palladium-silver alloy. They are preferably applied to the substrate 708 by printing. About 50 electrodes 701 and 50 electrodes 702 are, preferably, applied.

After printing the printable paste on the substrate, the substrate with the applied paste is dried, for example for about 15 minutes at 100° C. The sensor layer then is sintered on the substrate with the electrodes applied for about 1 hour at about 150° C., resulting in a layer 709 on the substrate 708.

The sensors made this way have a relatively low resistance of about 4 kOhms at 95% relative humidity. When the humidity drops to about 25%, the resistance rises to 16 kOhms. The linearity of such a sensor is excellent—see FIG. 1, which illustrates a sensor in which the base mixture has a relationship or proportion, by weight, of the respective components of 2:1:1.

The resistance is measured, as will appear below, not with permanent or continuous direct pulses, but with pulsed direct current, that is, pulses with intervening pulse gaps, or with pulses which change polarity and which may, but need not, have intervening pulse gaps. The curves of FIGS. 1–6 are derived with pulsed direct current.

The curves of FIGS. 1–6 illustrate the influence on the resistance by changing the respective proportion of the components of the basic mixture. FIG. 2 illustrates the relationship for 1:1:1. Dependence of resistance on relative humidity is observable only above about 70% relative humidity. The resistance range is even less than in the optimum weight relationship of 2 to 2.5:1:1 (FIG. 1), which may be of an advantage in some applications where it is only necessary to determine high humidity levels, that is, whether the humidity level has risen, for example if the humidity has changed from 70% humidity to 90% humidity. The resistance of the sensor at 90% humidity is even less than that of the sensor of FIG. 1, that is, between 6–8 kOhms.

FIG. 3 illustrates the response of the sensor to change in humidity for a weight proportion of 6:1:1. As can be seen, the resistance-humidity relationship is not linear, and beyond 70% relative humidity, there is little dependence of resistance on relative humidity—insufficient for obtaining suitable measurements. The resistance range of 50–300 kOhms is higher than in the optimum weight relationship (FIG. 1).

FIG. 4 illustrates the curve for a weight relationship of 8:1:1, more extreme than that of FIG. 3. It should be noted that such a sensor can hardly provide any useful output signals below 60% relative humidity. Measuring becomes extremely complex. The resistance range, between 200–2000 kOhms is even higher than in the prior examples.

If the proportion of chromium oxide is lowered with respect to the other components—see FIG. 5—there will be hardly any dependence of resistance on relative humidity. FIG. 5 illustrates a sensor with relative proportions—by weight—of 1:2:2, which, as seen in the graph, is flat. The resistance remains constant at about 4 kOhms.

Curves 2 to 5 illustrate that the bend of the characteristics depends highly on the chromium oxide component; lowering the resistance can be obtained by increasing the relative proportion of $V_2O_5$ and $Na_2WO_4$.

FIG. 6 illustrates an example which does not contain any $V_2O_5$ at all, and in which the relative weight relationships between chromium oxide and $Na_2WO_4$ is 2:1. The resistance between 40% and 100% relative humidity is very low and, effectively, independent of relative humidity. Between 30% and 40% relative humidity, a slight rise results and, below 30% relative humidity, a sharp rise occurs. This figure also illustrates that reduction of the resistance can be obtained by controlling the proportion of $Na_2WO_4$.

Generally, the sensor operates best with relative relationships, by weight, of the components $Cr_2O_3$, $V_2O_5$ and $Na_2WO_4$ in the range of between about 3:1:1 to 1.5:1:1; a relationship of 2.5:1:1 or 2:1:1 is preferred, with little difference in response between 2:1:1 and 2.5:1:1, but with slightly higher resistance levels with the higher proportion of chromium oxide. The sensor can easily be made by simple manufacturing steps, well known in the ceramic field and easily carried out on existing machinery. Application by thick-film technology is simple and also well known. The sensor with the proportions shown in FIG. 1, or approximately those proportions, has an essentially linear resistance - humidity characteristic, greatly facilitating evaluation of signals. The measuring sensitivity is good, since the sensor will be of comparatively low resistance. The sensor is essentially immune with respect to interference or noise or disturbance pulses, which is particularly important when the sensor is used in an automotive vehicle. The large number of electrical appliances and loads present in an automotive vehicle, peaks and other switching effects which occur therein, and a power supply of variable voltage depending, for example, on the charge state of the battery, additionally interfere with obtaining useful output data from sensor which are less rugged or more sensitive to disturbance or noise effects than the sensor as described and particularly of the composition shown in the curves of FIG. 1.

FIG. 8, schematically, illustrates placement of a sensor 812, for example of the structure of FIG. 7, within an automotive vehicle, connected by suitable connection lines coupled to the buses 705, 706, for example via an amplifier if necessary, to an evaluation circuit 813. The circuit 813, likewise can provide the supply energy, in pulse form, to the sensor. The sensor is installed within the passenger compartment 811 of an automotive vehicle 10.

Energy Supply for the Sensor 812 (FIGS. 7, 8), with reference to FIGS. 9–12

The sensor 812 is shown in FIG. 9, schematically, as resistance element 17. A direct current source 10 has its negative terminal 11 connected to ground or chassis of the vehicle 810, as schematically indicated by terminal 12 in FIG. 9. The positive terminal 13 of the source 10, shown schematically as a battery 25, is connected to a first terminal 14 of a controlled switch 15. The second terminal 16 of switch 15 is connected to a terminal of the sensor 17, the other terminal of which is connected to ground or chassis 12, and, further, to a signal input 18 of a sample-and-hold circuit 19. A pulse generator 20 provides a sequence of pulses, illustrated in the graph of FIG. 10. The pulse generator 20 is connected via line 21 to a junction which, in turn, is connected via line 22 to control the switch 15 and to an input 23 of the sample-and-hold circuit 19. The output 24 of the sample-and-hold circuit provides an output signal which will be representative of sensor resistance and, hence, of relative humidity.

Figure 10:
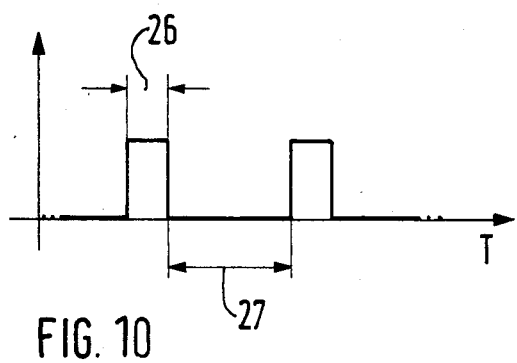
FIG. 10 is a pulse diagram illustrating the operation of the circuit of FIG. 9.

The pulse-time diagram of FIG. 10 illustrates the pulse sequence emitted by the pulse generator 20 as a function of time (T). The pulse duration 26, as well as the pulse gap or pause 27 are preset and determined by the output from the pulse generator 20.

BASIC OPERATION

The sensor 17, as described, operates on the basis of ion conductivity, that is, the ion conductivity of the sensor changes in relation to a physical parameter which is to be measured, which, in the example given, is relative humidity; temperature is another physical parameter with which an ion conductivity sensor can change its resistance. The conductivity—or, in other words, the resistance of the sensor 17—thus will be a measure of relative humidity. The conductivity is measured in a simple measuring circuit. A constant current, supplied by the source 10 which, in turn, is energized by the battery 25, will result in a voltage drop across the sensor 17 which will depend on the humidity. This voltage drop then can be sensed at terminals 24 and 12. For example, high ambient humidity will result in a low voltage drop. The constant measuring current, supplied by the constant current source 10, is connected in series with the humidity sensor 17. To avoid polarization effects, continuous d-c current should not be applied to the sensor 17. Thus, the electrically controlled switch is connected between the positive terminal 13 of the constant current source and the humidity sensor 17. Switch 15 is energized to provide the pulses shown in FIG. 10. The pulse duration 26 and the pulse gap 27 are fixed values. Suitably, pulse durations 26 are in the microsecond or millisecond range. the pulse gaps 27, preferably, are in the range of seconds. The voltage across the sensor 17, of course, is available only during the time duration of the pulses 26. A continuous output signal at terminal 24 can be obtained, however, by using a well known sample-and-hold circuit 19. A suitable sample-and-hold circuit 19 is described in "Electronic Circuits Manual", McGraw-Hill Book Company, 1971, page 691. This circuit receives the voltage at the signal input 18 during the pulse 26, stores the voltage in an internal analog memory—for example a capacitor—and provides this voltage at the output 24 until a new voltage value is applied to the input 18, to then replace the new voltage value at the output 24. To control the sample-and-hold circuit 19, input terminal 23 is connected to the pulse generator, so that the sample-and-hold circuit will carry out the sampling during the pulse 26; in other words, the circuit 19 is activated during the duration of the pulse 26. The negative flank at the end of the pulse 26 then triggers the storage of the voltage value at the input 18.

The constant current source 10 is supplied with external energy from a d-c power supply 25, for example the battery of the vehicle 810. Of course, the polarity which has been indicated can be reversed, that is, the indicated connection of the negative terminal 11 of source 10 to ground or chassis 12 can be reversed, so that the positive terminal 13 is connected to ground or chassis 12. The circuit has the advantage that only a single energy supply source with a single polarity output is needed.

Figure 11:
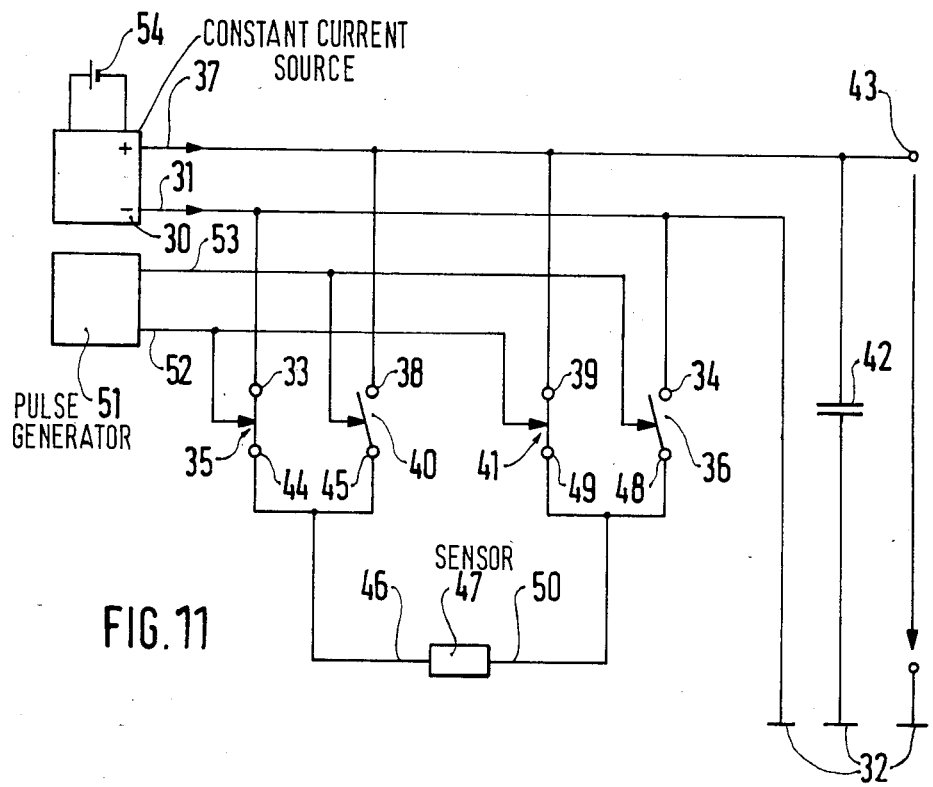
FIG. 11 is a schematic circuit diagram illustrating bipolar energization of the sensor.

The sample-and-hold circuit 19 is not strictly necessary. FIG. 11 illustrates a circuit with power supply to the sensor with changing polarity.

A current source 30 has its negative terminal 31 connected to ground or chassis 32; the negative terminal 31, further, is connected to a first terminal 33 of a controlled switch 35 and a first terminal 34 of a second controlled switch 36. The positive terminal 37 of current source 30 is connected to a first terminal 38 of a third controlled switch 40 and a first terminal 39 of a fourth controlled switch 41. A capacitor 42 is connected between the positive terminal 37 and ground or chassis 32. The output from the circuit is obtained across terminal 43 and ground or chassis 32. The second terminals 44, 45 of the first and third switches 35, 40 are connected to one terminal 46 of the humidity sensor 47. The second terminals 48 and 49 of the second and fourth switches 36, 41, respectively, are connected to the second terminal of the sensor 47. Pulse generator 51 generates two pulse sequences at respective output terminals 52, 53. The first pulse sequence shown in graph a of FIG. 12 controls the first and the fourth switches 35, 41. The second pulse sequence, shown in graph B of FIG. 12, controls the second and third switches 36, 40. A direct current energy source 54, for example a vehicle battery, provides direct current to the source 30.

Figure 12:
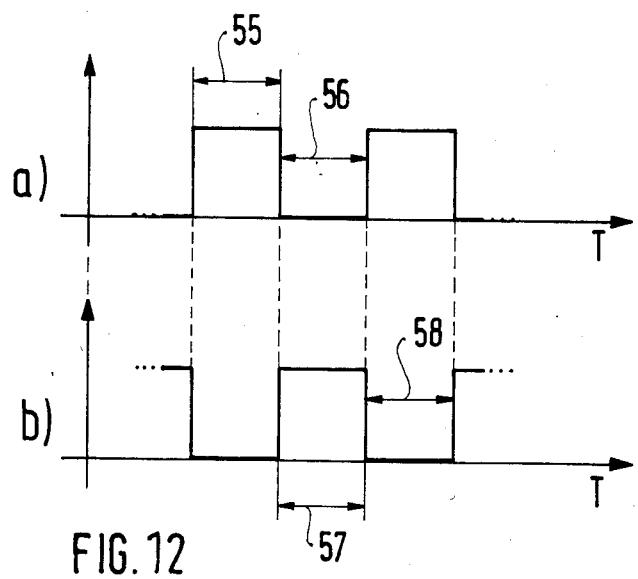
FIG. 12 illustrates the pulses being applied to the sensor in the circuit of FIG. 11.

The two pulse sequences on lines 52, 53, respectively, provided by the pulse generator 51 with respect to a function of time T are shown in FIG. 12. The pulse duration 55 and pause 56 of the pulses on line 53, as well as the pulse duration 57 and the pause 58 of the pulse sequence on line 53 see graph b, FIG. 12, are fixed values.

Operation, circuit of FIG. 11: The sensor 47 is connected by the four switches 35, 36, 40, 41 alternately between the two terminals 31, 37 or, in other words, between the two poles of the source 30. Source 30 is a constant current source. The drawing is shown with "chassis-negative" polarity. Terminal 43 provides the output signal of the circuit, with respect to ground or chassis 32. The signal is filtered by the capacitor 42, which, further, prevents possible voltage peaks which might arise upon switching operation of the four switches 35, 36, 40, 41 between the two output terminals or poles 31, 37 of the constant current source 30.

The pulses of the first and second pulse sequences, shown in graphs a and b of FIG. 12, are complementary. During the pulse duration 55 of the pulse illustrated in graph a, a pause 58 occurs on line 53 in the second pulse sequence, as seen in FIG. 12, and so on alternatingly. The pulses of the first pulse sequence as shown in graph a of FIG. 12 control the first and fourth switches 35, 41. In the position shown in FIG. 11, the switches 35, 41 are closed and, thus, terminal 46 of the sensor 47 is connected to the negative terminal 31 of the source 30 while terminal 50 of the sensor 47 is connected to the positive terminal of the source 30. The next pulse sequence as seen in graph b of FIG. 12 opens the closed switches 35, 41 and connects the switches 36, 40 to the sensor to apply the constant current to the sensor with reverse polarity. Within a cycle, formed by the pulse durations 55, 57 and the time of the pulse pauses 56, 58, constant current is supplied to the sensor 47 first in one, and then in the opposite direction. The average current value—with respect to time—will be zero if the pulse sequence of graph a and of the graph b of FIG. 12 are exactly equal. Of course, necessarily, the pulse pauses 56, 58 then also will be of equal length. The time duration for a cycle may be within the range of microseconds to milliseconds.

The direct current source 54, for example the battery of the vehicle 810, is connected to supply energy to the constant current source 30 which may be of any suitable and well known construction. Only a single polarity supply is needed.

The constant current source 10 (FIG. 9) or 30 (FIG. 11) may be a controlled constant current source, inherently providing pulsed output or reverse-polarity output, as seen graphically by the illustration of FIGS. 10 and 12, respectively. The sensors 17, 47, respectively, can then be connected directly to the outputs of the current source. Thus, the pulse generator 20 or the switching arrangement shown in FIG. 11 may be interposed between the respective batteries 25, 54 and the constant current sources 10, 30 to provide the respective outputs. The sensors then are connected directly to the constant current source terminals. In the embodiment of FIG. 9, source 10 will then be switched ON and OFF, in pulsed sequence as explained; in the embodiment of FIG. 11, the polarity of source 30 will change, in sequence, as explained.

The first, second, third and fourth switches 35, 36, 40, 41 of the embodiment of FIG. 11 preferably are integrated electronic circuit components, for example CMOS analog switches of the type CD4066. Of course, rather than using four switches 35, 36, 40, 41, which are only ON/OFF switches, two transfer switches with three terminals, respectively, may be used.

Rather than using a constant current source, like sources 10 and 30, constant voltage sources may be used. If so, the current flowing through the respective sensors 17, 47 will be representative of relative humidity. The circuit illustrated in FIGS. 9 and 11 further can be used with uncontrolled sources 10, that is, with neither a constant current nor a constant voltage source, by connecting a resistor in series with the sensor 17, 47, respectively, and the respective energy supply source. The functional relationship between measured voltage and relative humidity then must be corrected or normalized by a suitable network or calculating apparatus which normalizes the output values with respect to a given reference voltage or current.

Various changes and modifications may be made, and features described in connection with any embodiment of the invention may be used with any of the others; thus, the sensors 17, 47 need not have the composition exactly as shown in FIG. 1, but, rather, may have a composition which varies somewhat, in accordance with desired characteristics, as explained in connection with FIGS. 2 to 6. The sensor can be installed in a motor vehicle, at any location as desired.

We claim:

1. Method of making a relative humidity sensor to measure humidity by change of resistance between electrodes (701, 702) located on a substrate (708) in which a ceramic material is applied between the electrodes, comprising, in accordance with the invention, the steps of homogenizing a mixture of $Cr_2O_3$, $V_2O_5$ and $Na_2WO_4$;

presintering said homogenized mixture;

adding a glass paste to the presintered mixture to form an application paste;

applying said application paste on the substrate (708) between said electrodes (701, 702); and sintering the substrate, with the electrodes and the glass-presintered mixture thereon.

2. The method of claim 1, wherein said application step comprises printing said application paste on the substrate, with the electrodes applied thereon, by thick-film printing technology.

3. The method of claim 1, including the step of providing said mixture of $Cr_2O_3$, $V_2O_5$ and $Na_2WO_4$ in the proportion, by weight, of 1.5 to 3.0:1:1;

the presintering step comprises presintering at about 550° C.;

then grinding or milling the presintered material to a powder;

said step of adding a glass paste comprises adding about 10%—by weight—of glass paste;

and wherein said sintering step comprises sintering at a temperature of about 850° C.

4. The method of claim 3, wherein said step of providing the mixture comprises providing the mixture in a proportion, by weight, of 2 to 2.5:1:1.

5. The method of claim 4, wherein said substrate (708) comprises $Al_2O_3$, and the electrodes are interdigited electrodes (701, 702).

6. The method of claim 3, including the step of adding a thinner to the application paste to provide a printable application paste; and said application step comprises applying said printable application paste on the substrate with the electrodes thereon.

7. A humidity sensitive resistance ceramic mixture containing $Cr_2O_3$ and $V_2O_5$, wherein, in accordance with the invention, the ceramic mixture additionally contains $Na_2WO_4$.

8. The mixture of claim 7, wherein the components $Cr_2O_3$, $V_2O_5$ and $Na_2WO_4$ are present in the proportion of 1.5 to 3:1:1, by weight.

9. The mixture of claim 7, wherein the components $Cr_2O_3$, $V_2O_5$ and $Na_2WO_4$ are present in the proportion of 2 to 2.5:1:1, by weight.

10. Humidity sensor to determine the relative humidity comprising a substrate (708) of insulating material;

a plurality of interdigited double-comb electrodes (701, 702) located on the surface of the substrate;

and a humidity sensitive resistance mixture located at least between said electrodes, and sintered on the substrates and the electrodes, said humidity sensitive resistance mixture comprising a mixture containing $Cr_2O_3$ and $V_2O_5$, wherein, in accordance with the invention, the ceramic mixture additionally contains $Na_2WO_4$.

11. The sensor of claim 10, wherein the components $Cr_2O_3$, $V_2O_5$ and $Na_2WO_4$ are present in a proportion, by weight, of between about 3:1:1 to 1.5:1:1.

12. The sensor of claim 10, wherein the components $Cr_2O_3$, $V_2O_5$ and $Na_2WO_4$ are present in a proportion of to 2.5:1:1, by weight.

13. In an automotive vehicle, a humidity sensor to determine relative humidity within the passenger compartment (811) of the vehicle (810), wherein said humidity sensor comprises a substrate (708) of insulating material;

a plurality of interdigited comb electrodes (701, 702) located on the surface of the substrate;

and a humidity sensitive resistance mixture located at least between said electrodes, and sintered on the substrates and the electrodes, said humidity sensitive resistance mixture comprising a mixture containing $Cr_2O_3$ and $V_2O_5$, wherein, in accordance with the invention, the ceramic mixture additionally contains $Na_2WO_4$.

14. In an automotive vehicle, a humidity sensor to determine relative humidity within the passenger compartment (811) of the vehicle (810), wherein said humidity sensor comprises a substrate (708) of insulating material;

a plurality of interdigited comb electrodes (701, 702) located on the surface of the substrate;

and a humidity sensitive resistance mixture located at least between said electrodes, and sintered on the substrates and the electrodes, said humidity sensitive resistance mixture comprising $Cr_2O_3$, $V_2O_5$ and $Na_2WO_4$ present in a proportion of 2 to 2.5:1:1, by weight.

15. Method of sensing ambient relative humidity comprising providing a sensor (812, 17, 47) including a substrate (708);

a plurality of interdigited double-comb electrodes (701, 702) located on the substrate and defining, respectively, two output terminals (705, 706; 46, 50);

and a sintered, homogenized mixture of $Cr_2O_3$, $V_2O_5$ and $Na_2WO_4$, present in a proportion of, by weight, 1.5 to 3:1:1, positioned between the respective electrodes of the double-comb electrodes and sintered on the substrate, said method including the step of applying, cyclically sequential electrical current pulses to the terminals of the sensor, said pulses being of uniform polarity and spaced from each other by pulse gaps.

16. The method of claim 15, wherein the step of applying current pulses comprises applying the current pulses at a uniform, controlled constant current level.

17. Method of sensing ambient relative humidity comprising providing a sensor (812, 17, 47) including a substrate (708);

a plurality of interdigited double-comb electrodes (701, 702) located on the substrate and defining, respectively, two output terminals (705, 706; 46, 50);

and a sintered, homogenized mixture of $Cr_2O_3$, $V_2O_5$ and $Na_2WO_4$, present in a proportion of, by weight, 1.5 to 3:1:1, positioned between the respective electrodes of the double-comb electrodes and sintered on the substrate, said method including the step of applying, cyclically sequential electrical current pulses to the terminals of the sensor, said pulses being of alternatingly different polarity.

18. The method of claim 17, wherein the step of applying current pulses comprises applying the current pulses at a uniform controlled constant current level.

19. An ambient relative humidity sensing system comprising a humidity sensor including a substrate (708);

a plurality of interdigited double-comb electrodes (701, 702) located on the substrate and defining, respectively, two output terminals (705, 706; 46, 50);

and a sintered, homogenized mixture of $Cr_2O_3$, $V_2O_5$ and $Na_2WO_4$, present in a proportion of, by weight, 1.5 to 3:1:1, positioned between the respective electrodes of the double-comb electrodes and sintered on the substrate;

means (10, 20; 30, 51) coupled to said sensor terminals and supplying a constant current, in pulsed form, to said sensor (812, 17, 47); and means (24, 12; 43, 32) for deriving an output signal representative of current flow through the sensor and hence representative of relative humidity of ambient space to which said sensor is exposed.

20. The system of claim 19, wherein the pulsed current supplied to the sensor comprises unidirectional current pulses separated by pulse gaps or pulse pauses of sufficient duration to prevent polarization effects from occurring within the sensor.

21. The system of claim 19, wherein the pulsed current is in form of sequentially reversely polarized pulses.

22. A method of sensing an ambient condition comprising providing a sensor having sensor terminals, said sensor being sensitive to said ambient condition and including a substrate (708)

at least two electrodes (701, 702) located on the substrate;

an ion-conductive ceramic positioned between the respective electrodes and sintered on the substrate, said method including a step to avoid polarization effects due to current flow through the sensor comprising the step of applying cyclically sequential electrical current in form of unidirectional current pulses (26) separated by pulse gaps (27) to the terminals of the sensor;

and deriving an output signal representative of current flow through the sensor.

23. The method of claim 22, wherein the pulse gaps (27) are longer than the duration of the pulses.

24. The method of claim 22, wherein the duration of the pulses (26) is in the microsecond and millisecond range; and the duration of the pulse gaps (27) is in the range of seconds.

25. An ambient relative humidity sensing system comprising a sensor including a substrate (708);

at least two electrodes (701, 702) located on the substrate and defining, respectively, two terminals;

an ion-conductive ceramic sintered on the substrate and positioned between said electrodes; said ion-conductive ceramic comprising a ceramic mixture containing $Cr_2O_3$ and $V_2O_5$ and additionally containing $Na_2WO_4$;

means for applying an electrical current through the sensor, said current-applying means comprising means for avoiding polarization effects in the sensor due to current flow therethrough, said polarization effect avoidance means including means (10, 20; 30, 51) coupled to said terminals and supplying cyclically sequential constant current pulses (26) to the electrodes of said sensor; and means (24, 12; 43, 32) for deriving an output signal representative of current flow through the sensor and hence representative of the condition in the ambient space to which said ion-conductive ceramic is responsive.

26. The system of claim 25, wherein said means supplying the cyclically sequential constant current pulses apply unidirectional current pulses (26) to said terminals separated by pulse gaps, and wherein the duration of the pulses (26) is shorter than that of said pulse gaps (27).

27. The system of claim 25, wherein said means supplying the cyclically sequential constant current pulses apply to said terminals cyclically sequential pulses in which the polarity of sequential pulses is alternately reversed.

28. The system of claim 25, wherein the components $Cr_2O_3$, $V_2O_5$ and $Na_2WO_4$ are present in the proportion of 1.5 to 3:1:1, by weight.

29. The system of claim 25, wherein the components $Cr_2O_3$, $V_2O_5$ and $Na_2WO_4$ are present in the proportion of 2 to 2.5:1:1, by weight.

* * * * *